US006586427B2

(12) United States Patent
Hassan et al.

(10) Patent No.: US 6,586,427 B2
(45) Date of Patent: Jul. 1, 2003

(54) TREATMENTS FOR NERVOUS DISORDERS

(75) Inventors: Fred Hassan, Bridgewater, NJ (US); John Michael McCall, Kalamazoo, MI (US); Duncan Paul Taylor, Kalamazoo, MI (US); Philip F. Von Voigtlander, Plainwell, MI (US); Erik Ho Fong Wong, Portage, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/928,943

(22) Filed: Aug. 13, 2001

(65) Prior Publication Data

US 2002/0049230 A1 Apr. 25, 2002

Related U.S. Application Data

(63) Continuation of application No. 09/509,412, filed as application No. PCT/US99/04289 on Apr. 2, 1999, now abandoned.
(60) Provisional application No. 60/081,231, filed on Apr. 9, 1998.

(51) Int. Cl.$^7$ ............................................. A61K 31/535
(52) U.S. Cl. ............................... 514/231.2; 514/238.8; 514/239.2; 514/239.5
(58) Field of Search ..................... 514/239.2, 238.8, 514/239.5, 231.2

(56) References Cited

U.S. PATENT DOCUMENTS

| | | | |
|---|---|---|---|
| 4,229,449 A | 10/1980 | Meloni et al. | 424/248.58 |
| 5,068,433 A | 11/1991 | Meloni et al. | 564/349 |
| 5,391,735 A | 2/1995 | Meloni et al. | 544/174 |
| 6,046,193 A | 4/2000 | Heiligenstein | 514/239.2 |

FOREIGN PATENT DOCUMENTS

| | | |
|---|---|---|
| EP | 0 534 756 A2 | 3/1993 |
| EP | 0 721 777 A2 | 7/1996 |
| EP | 0 756 869 A2 | 7/1996 |
| WO | WO 96/12485 | 5/1996 |
| WO | WO 99/15177 | 4/1999 |
| WO | WO 99/52531 | 10/1999 |
| ZA | 93/0694 | 7/1993 |

OTHER PUBLICATIONS

A. Dubini et al., "Do noradrealine and serotonin differentially affect social motivation and behavior?", European Neuropyschopharmacology, vol. 7, Supp. 1, pp. s49–s55 (1997).

J. Elia et al., "Stimulant drug treatment of hyperactivity: Biochemical correlates," Clin Pharmacol Term, vol. 48, pp. 57–66 (1990).

R.J. Frances et al., "Alcohol and Other Psychoative Substance Use Disorders," The American Psychiatric Press Textbook of Psychiatry, 2d Ed., pp. 355–410 (1994).

D.R. Gastfriend et al., "Desipramine in the treatment of attention deficit order in adolescents," Psychopharmacology Bulletin, vol. 21, No. 1, pp. 144–145 (1985).

C. Kornetsky, "Psychoactive Drugs in the Immature Organism," Psychopharmacologia, vol. 17, pp. 105–136 (1970).

B.E. Leonard, "Noradrenaline in basic models of depression," European Neuropsychopharmacology, vol. 7, No. Suppl. 1, pp. s11–s16.

R.A. Pleak et al., "Effects of venlafaxine treatment for ADHD in a child," Am. J. Psychiatry, vol. 152, No. 7, p. 1099 (Jul. 1995).

C.W. Popper et al., "Disorders Usually First Diagnosed in Infancy, Childhood, or Adolescence," The American Psychiatric Press Textbook of Psychiatry, 2d Ed., pp. 729–832 (1994).

R.I. Shader, "Hypnosis," Manual of Physciatric Therapeutics, 2d Ed., pp. 81–85 (Chapter 11).

J. Svestka, "Antidepressives of the $3^{rd}$, $4^{th}$, and $5^{th}$ generation," Cesk–Phychiatr., vol. 90, No. 1, pp. 3–19 (Feb. 1994). (Czech).

P.H. Wender, "Hypnosis," Manual of Phyciatric Therapeutics, 2d Ed., pp. 167–179, (Chapter 18).

P.H. Wender et al., "A Controlled Study of Methyphenidate in the Treatment of attention Deficit Disorder, Residual Type, in Adults," Am. J. Psychiatry, vol. 142, pp. 547–552 (May 1985).

T.E. Wilens et al., "Pharmacotherapy of attention deficit hyperactivity disorder". Current opinions in CPNS Investigational Drugs, vol. 1 pp. 453–465 (1999).

T.E. Wilens et al., "Six–Week, Double–Blind, Placebo–Controlled Study of Desipramine for Adult Attention Deficit Hyperactivity Disorder," Am. J. Psychiatr,Y vol. 153, pp. 1147–1153 (Sep. 1996).

A.J. Zametkin et al., "Neurobiology of Attention Deficit Disorder With Hyperactivity: Where Have We Come in 50 Years?", J. Am. Academy Child Adolesc Psychiatry, vol. 26, pp. 676–686 (Apr. 1987).

A.J. Zametkin et al., "Noradrenergic Hypothesis of Attention Deficit Disorder with Hyperactivity: A Critical Review," Psychopharmacology: The Third Generation of Progress, pp. 837–842 (1987).

International Search Report in PCT/US99/04289 dated Sep. 13, 1999.

Written Opinion in PCT/US99/04289 dated Feb. 7, 2000.

*Primary Examiner*—Zohreh Fay
(74) *Attorney, Agent, or Firm*—Pharmacia & UpJohn Attorney; James D. Darnley, Jr.

(57) ABSTRACT

This patent application describes the treatment of Addictive disorders, Psychoactive Substance Use disorders, Intoxication disorders, Inhalation disorders, Alcohol addiction, Tobacco addiction and or Nicotine addiction; and Attention Deficit Hyperactivity Disorder (ADHD); comprising administering a therapeutically effective, nontoxic dose of Reboxetine and derivatives and or pharmaceutically acceptable salts thereof to a patient.

1 Claim, No Drawings

TREATMENTS FOR NERVOUS DISORDERS

CROSS REFERENCE TO RELATED APPLICATIONS

This is a continuation of U.S. patent application Ser. No. 09/509,412 filed Mar. 27, 2000 abandoned, which is the U.S. national phase of International Application No. PCT/US99/04289 filed Apr. 2, 1999, which claims the priority benefit of U.S. provisional patent application Serial No. 60/081,231 filed Apr. 9, 1998.

FIELD OF THE INVENTION

This invention describes new treatments for several nervous system disorders, including: Addictive Disorders, Psychoactive Substance Use Disorders, Nicotine Addiction or Tobacco Addiction resulting in Smoking Cessation and Attention Deficit Hyperactivity Disorder (ADHD). The treatment involves the administration of the drug Reboxetine to a patient in need.

BACKGROUND

The introduction of tricyclic antidepressants in the early 1960s has provided a major advance in the treatment of neuropsychiatric disorders. Reactive and endogenous depressions, diagnoses formerly carrying grave prognostic implications, have become, with the introduction of the tricyclics, manageable disorders with a much smaller toll on the patient and the society as a whole. Electroconvulsive Shock Therapy once the only efficacious treatment in spite of its highly invasive nature, has now become, thanks to tricyclics, an obsolete form of treatment in most Countries.

The early tricyclic compounds were reuptake inhibitors of all the catecholamines released in the synaptic cleft, thus resulting in prolongation and enhancement of the dopamine (DA), noradrenaline (NA) and serotonin (5-hydroxytryptamine=5-HT) action. Desipramine, for example, has been characterized as "one of the most studied of the tricyclic anti-depressants in ADHD children and adolescents." T. E. Wilens, et al. *Am. J. Psychiatry* 153:1147–1153, 1148 (1996). It has also been considered as a treatment for the disease in adults. Id. Unfortunately, a lack of selectivity for most tricyclics, including desipramine can also cause undesired side effects particularly on the acetylcholine (especially the muscarinic component), and histamine mediated neurotransmission.

Because of these unwanted pharmacodynamic activities, cognitive impairment, sedation, urinary and gastrointestinal tract disturbances, increased intraocular pressure were limiting factors in the clinical use of these compounds and often required discontinuation of treatment. Of utmost concern were also the cardiac toxic effects and the proconvulsant activity of this group of drugs.

Another drug, methylphenidate, is also known to have clinical efficacy for the treatment of ADHD. Wender, P. H., et al. *Am. J. Psychiatry* 142:547–552 (1985).

More recently, selective reuptake inhibitors for serotonin (SSRI) have been introduced with definite advantages in regard to fewer side effects without loss of efficacy.

Here we present the surprising finding that one particular drug from a new category of antidepressants, a so called noradrenaline (NA) reuptake inhibitor can be used to manage or treat a few special diseases, diseases having symptoms outside of what are usually considered depression symptoms. Now these diseases may be treated with Reboxetine.

SUMMARY OF THE INVENTION

This patent application describes the treatment of Addictive Disorders, Psychoactive Substance Use Disorders, Nicotine Addition or Tobacco Addiction (with a result of Smoking Cessation or a decrease in smoking) and Attention Deficit Hyperactivity Disorder (ADHD), comprising administering a therapeutically effective, nontoxic dose of Reboxetine and derivatives and of pharmaceutically acceptable salts thereof to a patient.

Reboxetine is the generic name of the pharmaceutical substance with the chemical name of 2-(I-((2-ethoxyphenoxy)benzyl)-morpholine, and its pharmaceutically acceptable salts. Reboxetine can be a free base, or it can include reboxetine methanesulfonate (also called reboxetine mesylate) or any other pharmaceutically acceptable salt that does not significantly affect the pharmaceutical activity of the substance.

A preferred dose range is 4 to 10 mg per patient per day and the most preferred dose is 6 to 8 mg or 8 to 10 mg per patient daily, depending upon the patient, delivered twice a day (b.i.d.).

ADDITIONAL DESCRIPTION OF THE INVENTION AND DESCRIPTION OF THE PREFERRED EMBODIMENT(S)

Reboxetine is the generic name of the pharmaceutical substance with the chemical name of 2-(I-((2-ethoxyphenoxy)benzyl)-morpholine, and its pharmaceutically acceptable salts. Reboxetine can be a free base, or it can include reboxetine methanesulfonate (also called reboxetine mesylate) or any other pharmaceutically acceptable salt that does not significantly affect the pharmaceutical activity of the substance. Reboxetine and a method of synthesis are described in U.S. Pat. No. 4,229,449, issued Oct. 21, 1980, Melloni et. al., incorporated by reference, methods of preparation are described in U.S. Pat. No. 5,068,433, issued Nov. 26, 1991, Melloni et. al. and in U.S. Pat. No. 5,391,735, issued Feb. 21, 1995, both incorporated by reference. Reboxetine may also be known under the trade name of EDRONAX™.

The pharmaceutical compositions and methods of administration described in U.S. Pat. No. 4,229,449 at col. 18, lines 33–66 are specifically incorporated by reference. Twice a day dosing is preferred with current formulations.

Reboxetine acts as an antidepressant. Antidepressants are frequently grouped into categories or "generations." The first generation of antidepressants were usually tricyclic antidepressants such as maprotiline that affected various neurotransmitter systems and are associated with many undesirable side effects. The second generation of antidepressants, such as mianserine, mirtrazapine and trazodone are largely devoid of anticholinergic action and their adrenolytic and antihistaminic effects are weaker. These are contrasted with the third generation of antidepressants (e.g. SSRI, ipsapirone, viloxazine, reboxetine, bupropione) that mediate only one of the three main neurotransmitter system for depression (5-HT, noradrenaline, dopamine) and they do not affect muscarine, histamine and adrenergic cerebral systems. Svestka, J. "Antidepressives of the 3rd, 4th and 5th generation," Cesk-Psychiatr. 1994 February; 90(1):3–19. (Czech).

Reboxetine however; does not act like most antidepressants. Unlike tricyclic antidepressants and even selective serotonin reuptake inhibitors (SSRIs), reboxetine is ineffective in the 8-OH-DPAT hypothermia test, indicating that reboxetine is not a selective serotonin reuptake inhibitor rather it is selective for the noradrenergic system. Thus, reboxetine is not an SSRI, rather it is considered a novel, selective, noradrenaline-reuptake inhibitor (NARI). Leonard-BE, "Noradrenaline in basic models of depression." European-Neuropsychopharmacol. Apr. 7, 1997, Suppl 1: S11-6; discussion S71-3. Unlike most drugs, Reboxetine is a highly selective norepinephrine uptake inhibitor, with only marginal serotonin and no dopamine uptake inhibitory activity. The compound displays only weak or no anti-cholinergic activity in different animal models and is devoid of monoamine oxidase (MAO) inhibitory activity.

Reboxetine is highly potent and fast acting. Our investigations indicate Reboxetine has potent antireserpine activity and combines the inhibitory properties of classical tricyclic antidepressants on the reuptake of noradrenaline with an ability to desensitize J-adrenergic receptor function without showing any appreciable interaction with muscarinic cholinergic and I-adrenerigic receptors. Moreover, Reboxetine shows less vagolytic activity than other tricyclic antidepressants.

The inventors have discovered that, because of its unique properties, Reboxetine has been found particularly useful for treating or enhancing the treatment of a few psychiatric symptoms or disorders, with greater efficacy and with fewer side effects, than are treated by known drugs. Furthermore, the inventors here have also discovered that Reboxetine can also be used to treat or to enhance the treatment of a few other specific psychiatric symptoms or disorders. The symptoms or disorders amenable to treatment with Reboxetine are provided below.

The dosage used to treat all of the disorders described here is as follows. Reboxetine is well tolerated and has a wide safety range, it can be administered in a dose range of active ingredient from about 1 to over 20 mg/kg. It is more commonly provided in dosages of from 1 to 20 mg per patient per day. The compound may be administered by any suitable method including a convenient oral dosage form. A preferred method is oral dosing twice a day. The preferred dose range is 4 to 10 mg per patient per day and the most preferred dose is 6 to 8 mg or 8 to 10 mg per patient daily, depending upon the patient, delivered twice a day (b.i.d.). It can also be given at dosages of 2, 4, 6, 8, 10 or 12 mg per patient per day or fractions thereof: For example, suitable administrations could be 4 mg in the morning and 2 or 4 mg in the evening or 6 mg in the morning and 4 mg in the evening. In some patients the ideal dosing would be 3–5 mg in the morning and 3–5 mg in the evening. A skilled practitioner would be expected to determine the precise level of dosing. The ideal dosing would be routinely determined by an evaluation of clinical trials and the needs of the patient.

The diseases described for treatment here are:

I. Addictive Disorders and Psychoactive Substance Use Disorders, such as Intoxication disorders, Inhalation disorders, Alcohol addiction, Tobacco Addiction and or Nicotine Addiction. Tobacco and Nicotine addiction would be treated with the goal of achieving either Smoking Cessation or Smoking Reductions Addictive Disorders, Alcohol and Other Psychoactive Substance Use Disorders, disorders related to Intoxication and Inhalants and especially Tobacco Addiction or Nicotine Addiction, may be treated with Reboxetine. Tobacco Addiction or Nicotine Addiction would be treated with Reboxetine in order to achieve smoking/chewing cessation or smoking/chewing reduction. General descriptions of Addictive Disorders, including disorders related to Intoxication and Inhalants and Tobacco Addiction or Nicotine Addiction may be found in many standard sources, such as, The American Psychiatric Press Textbook of Psychiatry, Second Edition, Edited by Robert E. Hales, Stuart C. Yudofsky, and John A. Talbott, copyright 1994, incorporated by reference, especially pp. 401 et. seq., section on "Nicotine" incorporated by reference. Another of many texts is the Manual of Psychiatric Therapeutics, Second Edition, edited by Richard I. Shader, incorporated by reference, especially pp. 85 from Chapter 11 (Hypnosis).

The treatment of Alcohol and Other Psychoactive Substance Use Disorders, such as disorders related to Intoxication and Inhalants and Tobacco Addiction or Nicotine Addiction but especially Tobacco Addiction involves the administration of Reboxetine in a manner and form that provide a reduction in the symptoms of the disease. Tobacco Addiction or Nicotine Addiction in particular would be treated to achieve a reduction or cessation of smoking or chewing of nicotine containing materials by a patient. Cessation or a reduction in smoking or chewing of addictive or psychoactive substances involves the administration of Reboxetine in a manner and form that provide a reduction in the symptoms of the disease, or with Tobacco or Nicotine with a reduction in the amount smoked or chewed. See the general description above for administration of Reboxetine.

II. Attention Deficit Hyperactivity Disorder (ADHD)

ADHD is a condition or disease state that may be treated with Reboxetine. General descriptions of ADHD, may be found in many standard sources, such as, The American Psychiatric Press Textbook of Psychiatry, Second Edition, Edited by Robert E. Hales, Stuart C. Yudofsky, and John A. Talbott, copyright 1994, incorporated by reference, especially pp. 741 et. al., section on "ADHD," incorporated by reference. Another of many texts is the Manual of Psychiatric Therapeutics, Second Edition, edited by Richard I. Shader, incorporated by reference, especially Chapter 18, Attention-Deficit hyperactivity Disorder, and pp. 172 et. seq., incorporated by reference.

The treatment of Attention Deficit Hyperactivity Disorder in children and adults involves the administration of Reboxetine in a manner and form that provide a reduction in symptoms of the disease. A child or young adult may require a smaller dosage depending upon the size, age, condition of the patient. See general description above for administration of Reboxetine.

What is claimed is:

1. A method of increasing a patient's attention span and calming a patient afflicted with attention deficit hyperactivity disorder, the method comprising the step of administering a therapeutically effective, nontoxic dose of reboxetine, reboxetine or pharmaceutically acceptable salts thereof to a patient.

* * * * *

UNITED STATES PATENT AND TRADEMARK OFFICE
CERTIFICATE OF CORRECTION

PATENT NO.    : 6,586,427 B2
DATED         : July 1, 2003
INVENTOR(S)   : Hassan et al.

It is certified that error appears in the above-identified patent and that said Letters Patent is hereby corrected as shown below:

Column 4,
Line 58, please delete "reboxetine or," and insert -- reboxetine derivatives, or -- in its place.

Signed and Sealed this

Eleventh Day of November, 2003

JAMES E. ROGAN
*Director of the United States Patent and Trademark Office*